United States Patent [19]

Warnke

[11] Patent Number: 4,573,449
[45] Date of Patent: Mar. 4, 1986

[54] METHOD FOR STIMULATING THE FALLING ASLEEP AND/OR RELAXING BEHAVIOR OF A PERSON AND AN ARRANGEMENT THEREFOR

[76] Inventor: Egon F. Warnke, Im Tannengrund 28, D-3002 Wedemark, Fed. Rep. of Germany

[21] Appl. No.: 473,353

[22] Filed: Mar. 8, 1983

[51] Int. Cl.$^4$ ............................................. A61N 1/34
[52] U.S. Cl. ..................................... 128/1 C; 128/422
[58] Field of Search .............................. 128/1 C, 422

[56] References Cited

U.S. PATENT DOCUMENTS

| | | | |
|---|---|---|---|
| 3,712,292 | 1/1973 | Zentmeyer, Jr. | 128/1 C |
| 3,835,833 | 9/1974 | Limoge | 128/1 C |
| 3,884,218 | 5/1975 | Monroe | 128/1 C |

FOREIGN PATENT DOCUMENTS

| | | | |
|---|---|---|---|
| 2536812 | 3/1977 | Fed. Rep. of Germany | 128/1 C |
| 2385409 | 12/1978 | France | 128/1 C |
| 2403802 | 5/1979 | France | 128/1 C |

*Primary Examiner*—Kyle L. Howell
*Assistant Examiner*—Ruth S. Smith

[57] ABSTRACT

A method and apparatus is provided with which a person suffering from sleeplessness can be more easily relaxed and may more rapidly fall asleep. In particular, sound pulses are emitted by an electro-acoustic transducer, according to the cadence of which, the person seeking to fall asleep is induced to breathe in and out over a predetermined period of time. By suitably selecting the pulse sequence frequency, the pitch and the amplitude of the sound pulses may be adjusted thereby enhancing the process of falling asleep.

2 Claims, 3 Drawing Figures

METHOD FOR STIMULATING THE FALLING ASLEEP AND/OR RELAXING BEHAVIOR OF A PERSON AND AN ARRANGEMENT THEREFOR

BACKGROUND OF THE INVENTION

The invention relates to a method for stimulating falling asleep and/or relaxing behavior of a person by means of an electronic arrangement.

From numerous medical publications as well as from daily life, it is known that more and more people suffer from sleeplessness and cannot find the right way to relax. There is a continually increasing consumption, in developed countries, of medicine for relaxing, in the form of so-called sleeping pills, despite the fact that such medicants have side effects and their effectiveness decreases with increased consumption.

However, many people do sleep without difficulties. By means of thorough testing and research, it has been ascertained that with effortless falling asleep without medication, certain cerebral currents (brain waves) change while, simultaneously, the pulse rate and the breathing rhythm is slowed down. It is furthermore known that by means of meditation exercises, the cerebral currents, the pulse rate and the breathing rhythm can be changed, so that a condition of increased relaxation, up to the point of falling asleep, can be attained. A known and simple meditation method consists in uniformly counting in a breathing rhythm; however, a certain amount of concentration is necessary. In practice, however, it has also been ascertained that such exercises, in particular by those persons who have, in any event, difficulties with relaxing and falling asleep, are very difficult to learn.

SUMMARY OF THE INVENTION

It is an object of the present invention to provide a method which, without medication and solely by means of outside influences on persons seeking to fall asleep, which influences are produced by means of an electronic arrangement, can enhance relaxation resulting in the person falling asleep.

In accordance with the invention, this object is achieved by means of a method with which, by direct influence, controlling of the breathing rhythm results by way of an electronic arrangement which produces pulses acting on at least one of the senses, visual or hearing, of a person in a rhythmic controlling of the breathing rhythm.

The method in accordance with the invention provides an electronic pulse emitter, which is preferably in the form of an electro-acoustic converter, acting on the auditory senses of a person seeking to fall asleep. The pulse emitter produces a sonic pulse sequence which corresponds to the breathing rhythm of a tired, but not yet sleeping, person. The person seeking to fall asleep is induced to adjust his (or her) breathing rhythm to that of the sonic pulse sequence.

The invention is based on the recognition that the breathing rhythm as well as the breathing rate of a person seeking to fall asleep can be stimulated by a so-called step-maker. The stimulation can be achieved by outside influence on the visual or hearing senses of the person. This influence may be effected by means of touch impulses which act on particularly sensitive areas of the skin, light impulses which act on the visual senses, or sound impulses which act on the auditory senses.

It has further been recognized that it can be particularly advantageous to divide, into a first and second partial impulse, individual sonic pulses for the breathing cycle by intermediate switching of a pulse pause, whereby the first partial impulse, at a first sound level, stimulates inhaling while the second partial impulse, at another sound level, stimulates exhaling.

A special embodiment of the method is based on the recognition that the breathing rate of a person going to sleep, continuously slows down. While a resting, but not yet sleeping, adult has a typical breathing cycle of about 5 seconds, the time of the breathing cycle of a sleeping person is about 7 seconds. Based on this fact resides the functioning of an arrangement for carrying out the method in which, by means of defined sound signals, the person seeking to fall asleep is first given, at a frequency of about 0.2 Hz, a breathing rhythm which then is continuously reduced, over a predetermined period of time, to a frequency of about 0.14 Hz. When the person seeking to fall asleep breathes in and out according to the sound emissions, his/her pulse rate and cerebral currents change, according to experience, continuously until they have reached the characteristic value for sleeping. In many cases, the difficulties for falling asleep can, in this way, be removed without medication.

At the beginning of the stimulation, two sounds of different tone quality appear at a uniform rhythm and constant intensity. The person seeking to fall asleep begins, with the higher sound, to quietly inhale and, with the following lower sounds, to quietly exhale. The pause between the two sounds is determined to behave somewhat like, as is usual, the normal breathing pattern. According to experience, it is furthermore helpful when, with decreasing stimulation frequency, the amplitude of the respective tone pulses also decreases.

DESCRIPTION OF THE DRAWINGS

Hereinafter there is described the method in accordance with the invention in a particular embodiment and in conjunction with a set of drawings, in which.

DESCRIPTION OF THE PREFERRED EMBODIMENT

Figure 1:
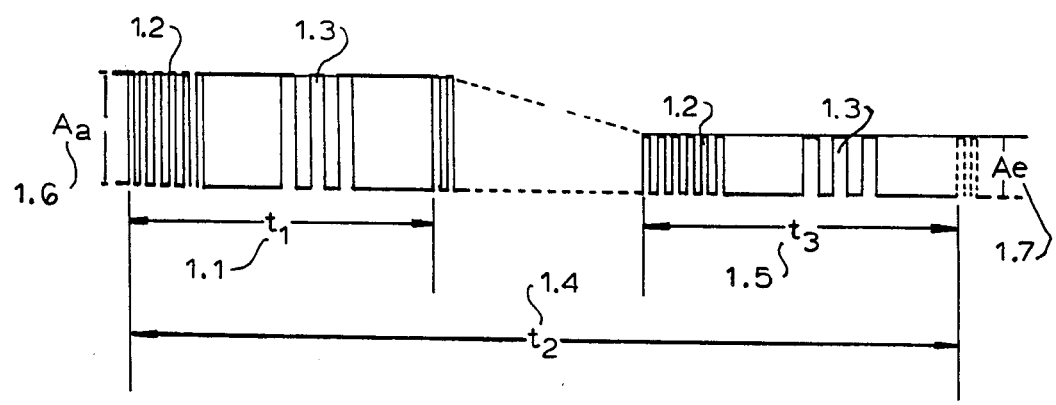
FIG. 1 illustrates a preferred sound pulse sequence.

In FIG. 1 there is illustrated the sound pulse sequence of an arrangement for carrying out the method. Reference number 1.1 indicates the time period $t_1$ for one breathing cycle. Within this time period of about 5 seconds, at the beginning of the stimulation, the inhalation pulse 1.2 is produced with a higher sound frequency than the exhalation pulse 1.3. In the time period $t_2$, designated by the reference number 1.4, there are contained about 300 breathing cycles, preferably 256 breathing cycles, it being demonstrated that a person seeking to fall asleep has indeed fallen asleep after about 256 breathing cycles. At the end of the stimulation, the time period for a breathing cycle $t_3$ is designated by the reference number 1.5, which breathing cycle has increased to approach a time period of about 7 seconds. The initial amplitude value $A_a$ is designated with the reference number 1.6 and has, at the end of the stimulation, been reduced to the amplitude value $A_e$, designated with the reference number 1.7.

Figure 2:
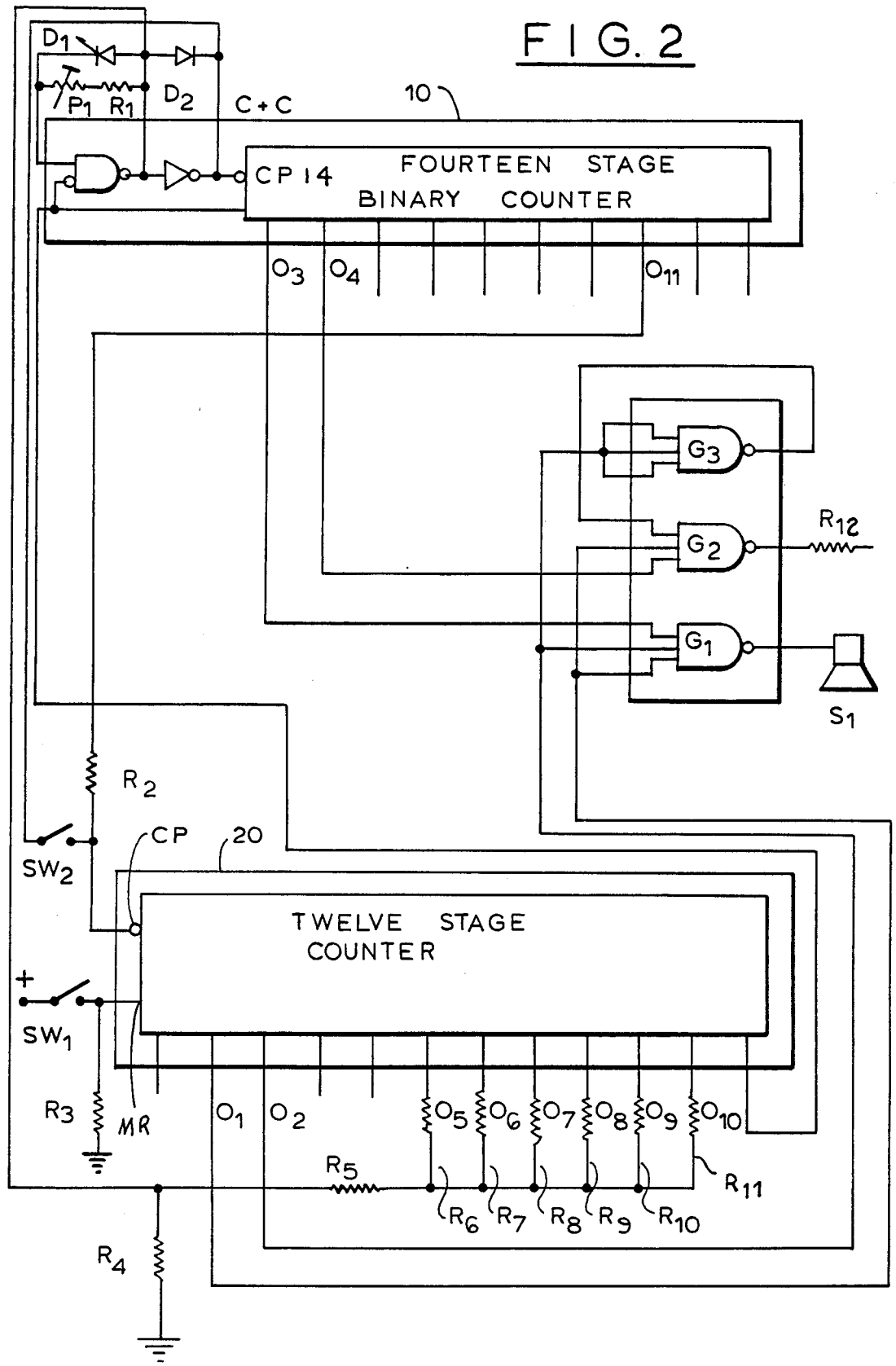
FIG. 2 illustrates a circuit diagram of an arrangement for carrying out the method.

FIG. 2 illustrates a practical embodiment of the invention. Basically, an oscillator is used to provide a signal in the frequency range from 5900 Hz to 7800 Hz, which signal is divided in a 14-stage binary counter 14. In the circuit shown, a counter/oscillator 10 is provided in a single integrated circuit, for example HEF 4060B, along with capacitance diodes D1 and D2, and a serial arrangement of a potentiometer P1 and a resistor R1 connected as shown.

Outputs $O_3$ and $O_4$ of the counter/oscillator 10 provide a first and a second tone signal, respectively, which are applied to respective first inputs of a pair of 3-input NAND-gates, G1 and G2. Output $O_{11}$ of the counter/oscillator 10 is coupled, via a resistor R2, to a clock input $\overline{CP}$ of a 12-stage binary counter 20, for example HEF 4040B. Output $O_1$ of this counter 20 in connected to a second input of both NAND-gates G1 and G2, while output $O_2$ of the counter 20 is connected to a third input of NAND-gate G2 and to the three interconnected inputs of a third 3-input NAND-gate G3, connected as an inverter, the output of NAND-gate G3 being connected to a third input of NAND-gate G1. The three NAND-gate G1, G2 and G3 may be arranged in a single integrated circuit, for example HEF 4023B.

A master reset MR of the counter 20 is connected to ground via a resistor R3 and to a positive terminal of a voltage source, not shown, via a start sensor switch SW1. The clock pulse input $\overline{CP}$ of counter 20 is further connected to an external capacitor connection $C_{tc}$ of counter/oscillator 10 via stop sensor switch SW2. The junction between diodes D1 and D2 is connected, via resistor R4, to ground and, via resistor R5, to outputs $O_5$, $O_6$, $O_7$, $O_8$, $O_9$ and $O_{10}$, respectively, through resistors R6, R7, R8, R9, R10 and R11, respectively. Finally, the outputs of NAND-gates G1 and G2 are intercconnected through a series arrangement of a resistor R12 and , for example, an electro-acoustic tranducer S1, for example Sennheiser HM21-34.

Typical values for the above components are as follows:

D1—BB909B
D2—BB909B
P1—2.2 Mohms
R1—3.3 Mohms
R2—1.2 Mohms
R3—5.1 Mohms
R4—3.9 Mohms
R5—3.3 Mohms
R6—4.7 Mohms
R7—2.4 Mohms
R8—1.2 Mohms
R9—620 kohms
R10—300 kohms
R11—150 kohms
R12—68 kohms
S1—5 kohms In operation, potentiometer P1 is adjusted such that a frequency of, for example, 6400 Hz appears at the clock pulse input CP of the counter in counter/oscillator 10 upon activation of the circuit. The circuit is started by momentarily closing switch SW1 applying a positive voltage pulse to the master reset MR of counter 20 causing all the outputs thereof to be set to logic "0". The logic "0" at the master reset input MR of counter/oscillator 10 activates the oscillator therein and releases the counter therein.

The 6400 Hz signal at the clock pulse input CP of the counter results in a 400 Hz signal at output $O_3$ and a 200 Hz signal at output $O_4$. A 1.6 Hz signal is then applied to clock pulse input $\overline{CP}$ of counter 20 which results in a 0.39 Hz signal at output $O_1$ and a 0.195 Hz signal at output $O_2$. The result of these signals applied to NAND-gates G1, G2, G3 causes the transducer S1 to produce the 400 Hz tone for 1.28 sec. followed by no signal for 1.25 sec. This is then followed by the 200 Hz tone for 1.25 sec. followed by no signal for 1.25 sec. Eventually, as signals are progessively applied from outputs $O_5$ through $O_{10}$, the oscillator frequency decreases resulting in respective decreases in the outputs of transducer S1, until a signal appears at output $O_{11}$ of counter 20 causing the counter in the counter/oscillator 10 to reset and latching the operation thereof. When an electro-acoustic transducer is used, the respective decreases in the frequencies of the signals applied thereto result in respective decreases in the amplitude of the sound impulses emitted therefrom.

Figure 3:
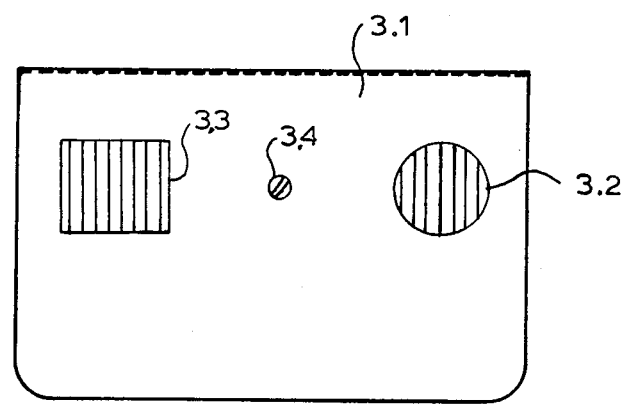
FIG. 3 illustrates a plan view of an embodiment of the invention.

FIG. 3 illustrates, in plan view, one possible packaging of the invention. The circuitry of FIG. 2 is mounted in a flat housing 3.1 made out of leather or a synthetic material. The start sensor switch SW1 is mounted behind the round opening 3.2 while the stop sensor switch SW2 is mounted behind the rectangular opening 3.3. Opening 3.4 allows access to the potentiometer for adjusting the basic frequency produced by the oscillator.

We claim:

1. A method for inducing relaxed behavior in a person comprising the steps:
   generating an oscillating signal;
   converting said signal to an audible pulse train sequence having a pulse repetition rate substantially equal to the breathing rate of a person on the verge of falling asleep;
   said audible pulse train sequence comprising two sounds of alternating frequency having a pause between them;
   gradually reducing the pulse repetition rate and alternating frequencies over time;
   instructing the person to inhale and exhale in time with the two sounds of alternating frequency; and
   terminating said pulse train after a predetermined time interval.

2. An apparatus for inducing relaxed behavior in a person, comprising:
   an oscillator connected to an electro-acoustic tranducer, a first counter means connected to said oscillator for determining the frequency of the signal from said oscillator to said electro-acoustic transducer, a second counter means connected to said first counter means and said electro-acoustic transducer by gate means such that the signal from said first counter means to said oscillator is intermittently interrupted;
   said first counter means being connected to said oscillator and said second counter means such that two different frequencies of said oscillator are alternately applied to said electro-acoustic transducer and such that the two different frequencies of said oscillator decrease over time;
   said second counter means connected to said first counter length of the interruption to increase over time until the signal produced at said electro-acoustic transducer terminates.

* * * * *